United States Patent [19]

Cramp et al.

[11] Patent Number: 4,560,248

[45] Date of Patent: Dec. 24, 1985

[54] FIBRE OPTIC SENSOR WITH BONDED DYE

[75] Inventors: John H. W. Cramp, St. Helens; Robert T. Murray, Helsby; Robert F. Reid, Highworth; Roy M. Mortier, Whitefield, all of England

[73] Assignee: Imperial Chemical Industries, PLC, London, England

[21] Appl. No.: 406,521

[22] Filed: Aug. 9, 1982

[30] Foreign Application Priority Data

Aug. 14, 1981 [GB] United Kingdom ............... 8124939

[51] Int. Cl.$^4$ .................... G02B 6/00; G02B 6/14
[52] U.S. Cl. .................... 350/96.34; 350/96.10; 350/96.29; 8/541; 8/542; 8/543; 356/402; 356/412; 356/432; 128/633; 128/634; 128/636
[58] Field of Search ............... 128/630, 632, 633, 634, 128/636

[56] References Cited

U.S. PATENT DOCUMENTS

| | | | |
|---|---|---|---|
| 2,963,338 | 12/1960 | Bailey et al. | 8/523 |
| 3,744,295 | 7/1973 | Allinikov | 427/8 |
| 3,904,373 | 9/1975 | Harper | 23/253 TP |
| 4,050,895 | 9/1977 | Hardy et al. | 350/96.10 |
| 4,075,493 | 2/1978 | Wickersheim | 250/461 R |
| 4,134,722 | 1/1979 | Swidler et al. | 8/541 |
| 4,137,060 | 1/1979 | Timmermann | 350/96.18 |
| 4,200,110 | 4/1980 | Peterson et al. | 128/634 |
| 4,204,866 | 5/1980 | Horak et al. | 250/227 |
| 4,403,826 | 9/1983 | Presby | 350/96.30 |

FOREIGN PATENT DOCUMENTS

| | | | |
|---|---|---|---|
| 0061884 | 10/1982 | European Pat. Off. | 350/96.10 |
| 2009394 | 7/1935 | United Kingdom | 350/96.10 |
| 2037448 | 4/1936 | United Kingdom | 350/96.29 |
| 2060871 | 11/1936 | United Kingdom | 350/96.10 |
| 2062877 | 12/1936 | United Kingdom | 350/96.29 |
| 1289146 | 9/1972 | United Kingdom | 73/335 |
| 1515089 | 7/1975 | United Kingdom | 350/96.29 |
| 0718767 | 9/1978 | U.S.S.R. | 356/402 |

OTHER PUBLICATIONS

Merck et al, "The Merck Index", 9th Ed., Merck and Co., 1976, p. 6374.

Primary Examiner—William L. Sikes
Assistant Examiner—Brian M. Healy
Attorney, Agent, or Firm—Cushman, Darby & Cushman

[57] ABSTRACT

For detecting changes in chemical or physical parameters an optical fibre core has bonded to its surface a chromophore responsive to the parameter. The core preferably has a porous surface with the chromophore coating extending into the porous structure.

10 Claims, 3 Drawing Figures

FIBRE OPTIC SENSOR WITH BONDED DYE

BACKGROUND OF THE INVENTION

This invention relates to sensors for detecting changes in chemical or physical parameters, using optical fibres and techniques associated therewith.

Optical fibres consist essentially of a transparent core surrounded by a thin protective cladding. The latter is in the form of a coating of lower refractive index than the core, and light fed into the core is transmitted along the fibre through the core being internally reflected at the core/cladding interface. The cores are usually of silica fibres, but other materials such as organic polymers may also be used, an essential requirement for the core being transparency at the wavelength of the light used.

SUMMARY OF THE INVENTION

According to the present invention, a sensor for detecting changes in a chemical or physical parameter comprises an optical fibre core to the surface of which is chemically bonded a chromophore responsive to the parameter.

The sensor of the invention may be used in the manner of known sensors by coupling to conventional optical fibres at both ends, one end leading to a light source, the other to a detector; the present sensor thereby forming an intermediate portion of the optical fibre. The sensor can also be constructed as an integral part of the length of fibre ab initio, either by omitting the cladding from an intermediate portion and bonding the chromophore to the core surface within that portion left bare, or by removing the cladding from an intermediate portion and bonding the chromophore to the surface in its place, as before. However, preparation of a sensitive intermediate portion in this manner is not always easy to achieve, especially when using a porous surface as described hereinbelow, and more generally we prefer to make the sensor separately, e.g. as an extended length which is thereafter cut to form shorter pieces for individual sensors. These shorter lengths can then be welded or coupled to conventionally clad fibres to enable light to be fed to the sensor and thence to a detector.

An alternative is to make one end of the sensor reflective, either directly by flattening and silvering the end or indirectly by coupling the end to a reflective device, so that light supplied to the sensor passes through it in both directions to be picked up by the supply fibre or by an adjacent separate fibre, and led to a detector. In this manner the sensitive intermediate portion is located adjacent one end of the fibres, and it is preferred to use this configuration when making the sensor in situ as an integral part of a conventional fibre. Such reflective sensors may be more sensitive per unit length due to the passing of the light in both directions, but conventional means for splitting out the light for the detector from the common carrier tends to waste a portion of the light. Nevertheless, a reflective sensor on the end of a single optical fibre can provide a very fine sensory probe, the sensor itself being substantially the thickness of only an optical fibre core.

Our preferred chromophores are dye molecules, whose colours are sensitive to the parameter. Examples include dyes whose colours change with pH for use in pH sensors, other dyes and complexing agents are sensitive to specific chemicals such as metal ions and may be similarly employed. Physical parameters such as temperature may be measured by luminescent dyes, e.g. where intensity of fluorescence varies as a function of temperature. Other chromophores include enzymes which change colour in the presence of specific biological species.

Our preferred cores are glass fibres, to which dye molecules can conveniently be coupled using intermediate silane coupling agents, having a silane functional group with affinity for the glass core and a group reactive with the chromophore. For example, the known silane coupling agent $NH_2CH_2CH_2CH_2Si(OC_2H_5)_3$ will chemically bond to the glass fibre, and the amino group extends from the glass surface to be available for coupling with an acidic group, e.g. an acidic chlorine, of a dye molecule. However, in selecting a dye on account of its having a colour change at a specific desired pH, it is naturally important that the group reactive with the silane is not part of the colour producing conjugation such as to destroy the desired chromophetic effect. One preferred way of making a suitable indicator dye for linking to the silane coupling agent described above, is to link a chloro-s-triazine ring directly to the dye molecule. The chlorine bonds on the triazine ring will allow coupling of the dye, via the triazine ring, onto the amine unit of the silane coupling agent.

We have found that the amount of dye which can be bonded in this way to the surface of a normal silica core tends to be insufficient to detect changes in colour without particularly sensitive detectors or particularly long lengths of sensing fibre. For this reason we prefer that the surface to which the chromophore is bonded, be a surface of a porous material and include at least some of the surface area within the pores. We find that we can thereby greatly enhance the sensitivity of the sensor. However where the whole core is porous the loss of light due to scattering can be severe. A preferred sensor is one wherein the core comprises a non-porous portion surrounded by a porous layer to which the chromophore is bonded.

The surrounding porous layer can be integral with the non-porous portion which it surrounds, being formed by etching a substantially non-porous fibre. For a glass fibre core, this may be achieved by exposing the core to hydrogen fluoride gas followed by treatment with acid. However, we find this method is difficult to control, and prefer a sensor wherein the optical fibre core is a composite of a non-porous material surrounded by and in intimate contact with a layer of porous material. This can be achieved, for example by coating the core with an outer layer of a porous glass, or of a glass that can be made porous. For example, a glass fibre may be coated with a layer of a silica glass doped with a predetermined amount of sodium borate, which is acid soluble. Heat treatment of this doped glass forms borate-rich areas in the glass which can be etched out with acid to remove the borate, leaving behind a porous outer layer around the core. This enables chromophore molecules to be bonded by silane coupling agents within the interstices of this porous layer.

Whether the outer porous layer is formed by making an outer layer of a homogeneous fibre porous or by making porous an applied layer of a different material, we generally prefer when connecting one or both ends of a sensor comprising a homogeneous inner portion surrounded by an outer porous layer to an optical fibre comprising a core coated with a conventional cladding, that the diameter of the inner portion of the sensor be substantially the same as the core of the optical fibre. This matching is to minimise losses at the fibre/sensor interface. Where there is disparity, lenses may be inserted in known manner between the fibre and sensor.

One possible exception to the above generalisation is when the sensor is formed in situ adjacent to the end of a normally clad optical fibre, the end of which, i.e. beyond the integral sensor, is made reflective. This provides a simple and convenient form of manufacture, which appears to be more tolerant to its inevitable mismatch of core diameters, possibly due to a less abrupt change in the depth of porosity where the cladding ends, and possibly due also to the avoidance of any join between sensor and fibre.

The present sensors are particularly suitable for forming the basis of a sensing probe, e.g. for use in industial or medical applications. Such probes typically comprise a sensor and fibre optic means for launching light into the sensor and for collecting the light or modification thereof after it has been transmitted through at least part of the sensor. The light may be caused to travel through the sensor in a single direction by launching the light in at one end and collecting it at the other. Alternatively, by making the sensor reflective at one end, and both launching and collecting from the other end the probe can be formed with a terminal sensor. Optical fibres which can be used for the fibre optic means and the various ways in which they can be coupled to the sensor, include those described for general applications hereinabove.

Chromophores which are sensitive to the parameters through chemical reaction with their environment, necessarily require direct contact with that environment. In most instances this precludes the use of a protective cladding around the core, whether that core be homogeneous or a composite core, and in this the fibres forming the sensors differ from the optical fibres normally used to convey light without significantly changing it (other than some attenuation). Even where claddings are known which are permeable to the particular environment, they may significantly lengthen the response time by restricting access to the underlying chromophore-containing layers, especially where such layers are themselves porous.

The optical fibre core to which the chromophores are bonded is preferably of circular cross section, this being generally the easiest and cheapest to make, and also more readily matches the circular cross sections of conventional optical fibres used to convey light to and from the sensor, thereby minimising loss at the interface. Fibres of other cross sections, such as flattened tape, can also be used in the present sensor, but generally only with lower efficiencies and higher costs.

BRIEF DESCRIPTION OF THE DRAWINGS

The invention is illustrated by the accompanying drawings of three embodiments thereof, wherein.

DESCRIPTION OF THE PREFERRED EMBODIMENTS

Figure 1:
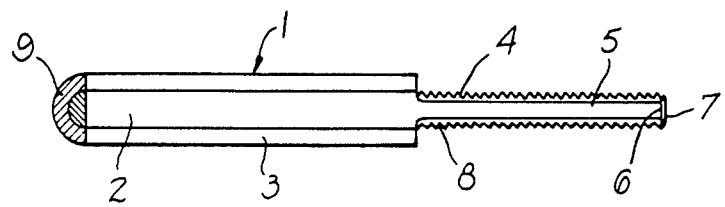
FIG. 1 is a section through a terminal sensor.

In FIG. 1, one end of an optical fibre 1 comprises a core 2 and a cladding 3. The core extends beyond the end of the cladding, and the outer layer 4 of the extended portion has been made porous. The porous outer layer surrounds a homogeneous inner portion 5. The terminal surface 6 of the fibre is an optical plane and has a reflective coating 7. The porous layer has been treated with a silane coupling agent and reacted with a pH sensitive dye, to give a sensitivity throughout the porosity and is represented in the drawing by a thickened line 8. The optical fibre extends away from the sensitive end beyond the cut end 9 shown, to be connected to appropriate light source and detector, e.g. in known manner.

Figure 2:
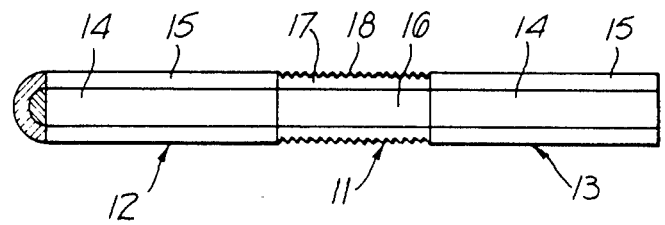
FIG. 2 is a section through a sensor joined into an optical fibre.

FIG. 2 shows a sensor 11 according to the invention, stuck between the ends of two conventional optical fibres 12, 13 e.g. using an adhesive. The two optical fibres, which both comprise a core 14 and a cladding 15, extend beyond the cut ends shown in the drawing, and are connected to an appropriate light source and detectors respectively. The sensor comprises a homogeneous inner portion 16 which is substantially the same as the cores of the fibres on either side, both in composition and diameter. Around this inner portion is an outer layer 17 of porous glass, which has been treated with a chromophore, bonded to the glass by a silane coupling agent. This sensitive layer extends throughout the thickness of the porous outer layer 17, but is shown in the drawing as the thickened wavy line 18.

Figure 3:
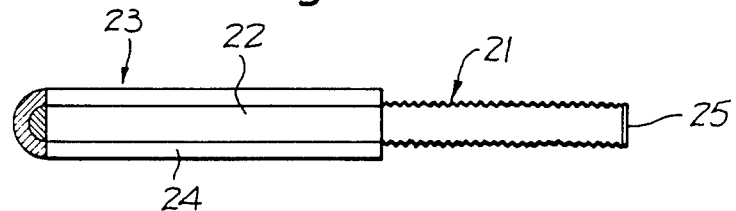
FIG. 3 is a section through an alternative to the sensor of FIG. 1.

FIG. 3 shows the end of a probe having a terminal sensor 21 secured to the core 22 of an optical fibre 23 used to transmit light to and from the sensor. The transmissive fibre has a cladding 24, but the sensor does not. The sensor is porous throughout, being formed from a length of porous fibre which is impregnated with a dye bonded to the glass surface throughout the pores. The terminal surface 25 of the sensor is made reflective so that light launched into the sensor by the fibre 23 travels through the sensor and is reflected back to the fibre from the terminal surface 25. On passing through the sensor, the light is modified according to the state of the dye and partly attenuated by scattering.

We claim:

1. An optical sensor comprising an optical fibre core and a sensitive chromophore chemically bonded to the surface of the said core, the chromophore being variable in colour, in response to changes in a predetermined chemical or physical parameter, in combination with fibre optic means for launching light into the sensor and for collecting the light after it has been transmitted through the sensor; whereby on being passed through the sensor, light is modified according to the colour response of the chromophore to the parameter to which the chromophore is sensitive.

2. A sensor as claimed in claim 1 wherein the surface is of a porous material and includes at least some of the surface area within the pores.

3. A sensor as claimed in claim 2 wherein the core comprises a non-porous portion surrounded by a porous layer to which the chromophore is bonded.

4. A sensor as claimed in claim 3 wherein the porous layer is integral with the non-porous portion.

5. A sensor as claimed in claim 3 wherein the optical fibre core is a composite of a non-porous material surrounded by and in intimate contact with a layer of porous material.

6. A sensor as claimed in claim 1, wherein the chromophore is a dye molecule whose colour is responsive to the parameter.

7. A sensor as claimed in claim 6 wherein the parameter is pH.

8. A sensor as claimed in claim 1, wherein the material forming the surface to which the chromophore is bonded is a silicate glass, and the chromophore is bonded to the glass through an intermediate silane coupling agent comprising a silane functional group with affinity for the glass and a group reactive with the chromophore.

9. A sensor as claimed in claim 8 wherein the chromophore is a dye molecule linked to the silane coupling agent via a triazine ring.

10. A sensor as claimed in claim 1 and forming a terminal portion of the fibre optic probe.

* * * * *